US012653480B2

(12) United States Patent
Qi et al.

(10) Patent No.: US 12,653,480 B2
(45) Date of Patent: Jun. 16, 2026

(54) METHOD AND APPARATUS FOR PERFORMING SINGLE GATING IN POSITRON EMISSION TOMOGRAPY SYTEMS

(71) Applicants: THE REGENTS OF THE UNIVERSITY OF CALIFORNIA, Oakland, CA (US); CANON KABUSHIKI KAISHA

(72) Inventors: Wenyuan Qi, Vernon Hills, IL (US); Li Yang, Vernon Hills, IL (US); Jeffrey Kolthammer, Vernon Hills, IL (US); Yu-Jung Tsai, Vernon Hills, IL (US); Evren Asma, Vernon Hills, IL (US); Maria Iatrou, Vernon Hills, IL (US); Jinyi Qi, Oakland, CA (US); Tiantian Li, Oakland, CA (US)

(73) Assignees: THE REGENTS OF THE UNIVERSITY OF CALIFORNIA, Oakland, CA (US); CANON KABUSHIKI KAISHA, Tokyo (JP)

( * ) Notice: Subject to any disclaimer, the term of this patent is extended or adjusted under 35 U.S.C. 154(b) by 302 days.

(21) Appl. No.: 18/336,807

(22) Filed: Jun. 16, 2023

(65) Prior Publication Data
US 2024/0225585 A1     Jul. 11, 2024

Related U.S. Application Data

(60) Provisional application No. 63/479,048, filed on Jan. 9, 2023.

(51) Int. Cl.
*A61B 6/00* (2006.01)
*A61B 6/03* (2006.01)

(52) U.S. Cl.
CPC .............. *A61B 6/541* (2013.01); *A61B 6/037* (2013.01)

(58) Field of Classification Search
CPC ................................ A61B 6/541; A61B 6/037
See application file for complete search history.

(56) References Cited

U.S. PATENT DOCUMENTS

2009/0253980 A1     10/2009  Wollenweber et al.
2012/0237099 A1      9/2012  Hara et al.
                    (Continued)

FOREIGN PATENT DOCUMENTS

JP          2012187350 A     10/2012

OTHER PUBLICATIONS

Extended European Search Report issued May 24, 2024 in corresponding European Patent Application No. 24150980.1, 10 pages.
                    (Continued)

*Primary Examiner* — Joel F Brutus
(74) *Attorney, Agent, or Firm* — Oblon, McClelland, Maier & Neustadt, L.L.P.

(57)          ABSTRACT
A method for performing single gating in a positron emission tomography (PET) system includes: receiving list-mode data acquired by scanning an imaging object using the PET system, the list-mode data being affected by quasi-periodic motion of the imaging object; producing a plurality of vectors based on the received list-mode data; generating a reference vector based on the produced plurality of vectors; selecting, from the produced plurality of vectors, a set of vectors corresponding to a single gate, based on respective differences compared with the generated reference vector; and generating an image of the imaging object based on the selected set of vectors.

18 Claims, 13 Drawing Sheets

(56)            References Cited

U.S. PATENT DOCUMENTS

| | | | |
|---|---|---|---|
| 2012/0275657 A1* | 11/2012 | Kolthammer | A61B 6/037 |
| | | | 382/107 |
| 2015/0289832 A1 | 10/2015 | Bal et al. | |
| 2019/0133542 A1 | 5/2019 | Li et al. | |
| 2020/0134886 A1 | 4/2020 | Tsui et al. | |
| 2020/0393579 A1* | 12/2020 | Feng | G06T 11/003 |
| 2021/0065412 A1* | 3/2021 | Feng | G06T 11/005 |
| 2021/0181282 A1 | 6/2021 | Deller et al. | |
| 2021/0239863 A1* | 8/2021 | Tavitian | G06T 11/008 |
| 2022/0148236 A1 | 5/2022 | Bharkhada et al. | |
| 2022/0207792 A1 | 6/2022 | Feng et al. | |

OTHER PUBLICATIONS

S. Fürst et al., "Motion Correction Strategies for Integrated PET/MR," The Journal of Nuclear Medicine, vol. 56, No. 2, Jan. 8, 2015, pp. 261-269.

Woo Hyun Nam et al., "Motion-compensated PET image reconstruction with respiratory-matched attenuation correction using two low-dose inhale and exhale CT images," Physics in Medicine and Biology, Institute of Physics Publishing, vol. 58, No. 20, Sep. 27, 2013, pp. 7355-7374.

* cited by examiner

300

S310 Receive list-mode data acquired by scanning the imaging object

S320 Segment the list-mode data into mini frames of a short temporal length (e.g., 0.1s)

S330 Produce mini vectors based on the mini frames

S340 Obtain a respiratory waveform of the imaging object

S350 Select a set of mini vectors for a single gate, based on the respiratory waveform

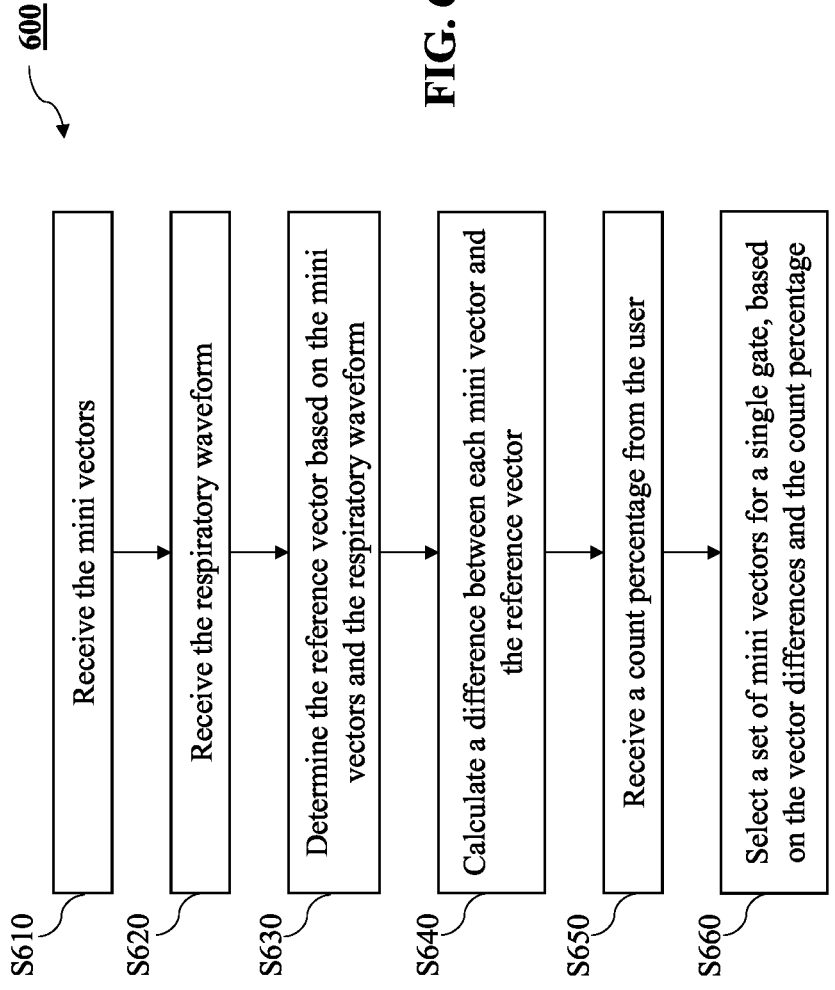

600

S610 Receive the mini vectors

S620 Receive the respiratory waveform

S630 Determine the reference vector based on the mini vectors and the respiratory waveform S640 Calculate a difference between each mini vector and the reference vector S650 Receive a count percentage from the user S660 Select a set of mini vectors for a single gate, based on the vector differences and the count percentage

FIG. 6

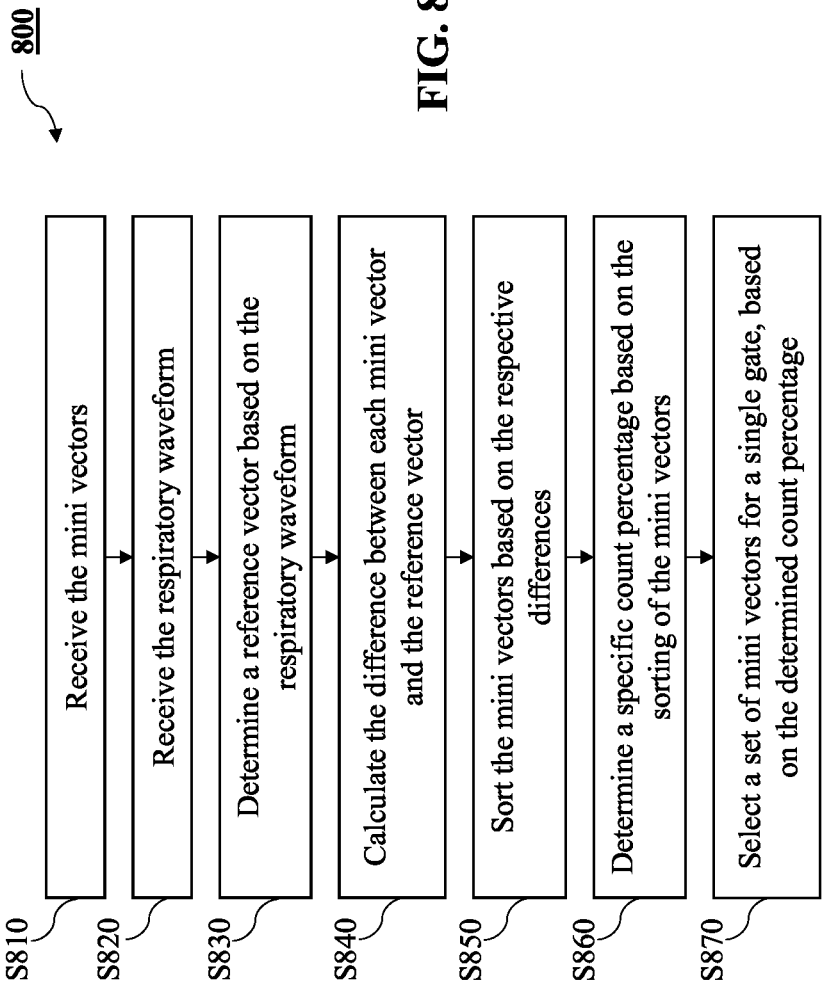

800

S810 Receive the mini vectors

S820 Receive the respiratory waveform

S830 Determine a reference vector based on the respiratory waveform

S840 Calculate the difference between each mini vector and the reference vector

S850 Sort the mini vectors based on the respective differences

S860 Determine a specific count percentage based on the sorting of the mini vectors S870 Select a set of mini vectors for a single gate, based on the determined count percentage

FIG. 8

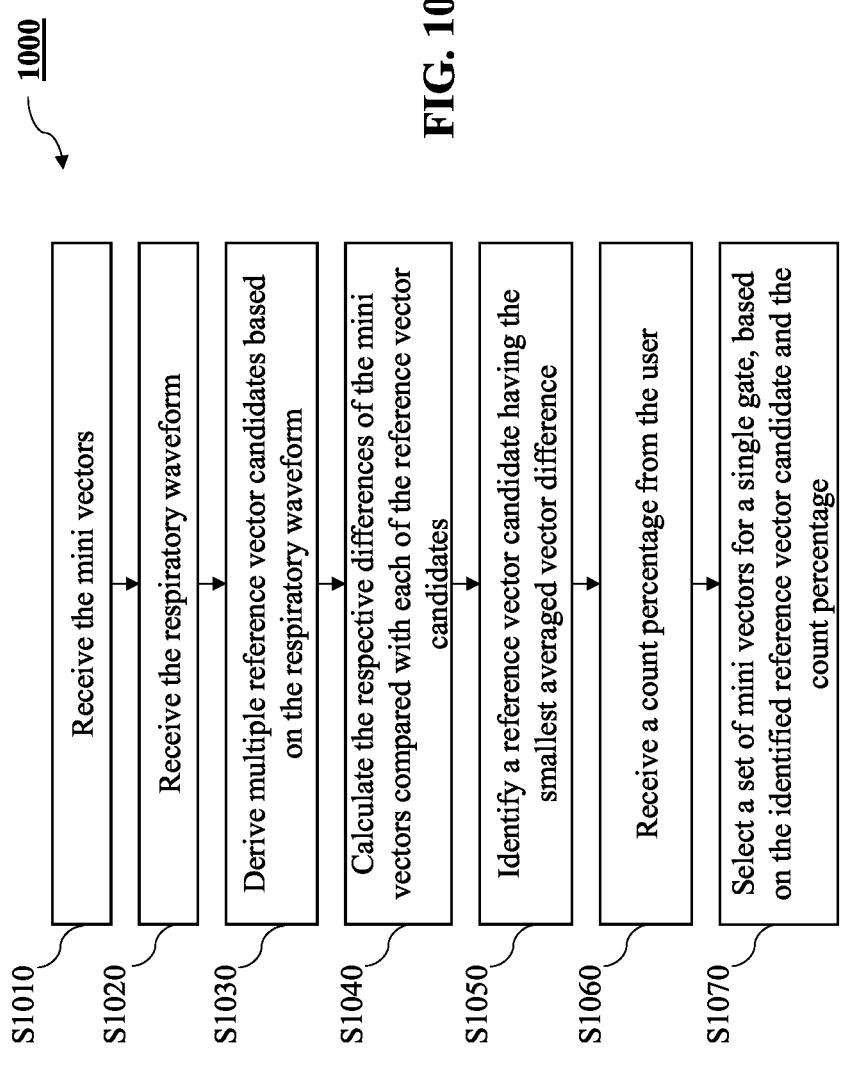

S1010 — Receive the mini vectors

S1020 — Receive the respiratory waveform

S1030 — Derive multiple reference vector candidates based on the respiratory waveform S1040 — Calculate the respective differences of the mini vectors compared with each of the reference vector candidates S1050 — Identify a reference vector candidate having the smallest averaged vector difference S1060 — Receive a count percentage from the user S1070 — Select a set of mini vectors for a single gate, based on the identified reference vector candidate and the count percentage

METHOD AND APPARATUS FOR PERFORMING SINGLE GATING IN POSITRON EMISSION TOMOGRAPY SYTEMS

CROSS REFERENCE TO RELATED APPLICATIONS

The present application claims priority to U.S. Provisional Application No. 63/479,048, entitled "Auto single respiratory gate by deep data driven gating for PET," filed on Jan. 9, 2023. The U.S. Provisional Application is incorporated herein by reference in its entirety.

FIELD

This disclosure relates to list-mode data gating in positron emission tomography (PET) systems as a means to eliminate motion-related inaccuracies and improve image quality in PET imaging.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Patient motion is a main source of blurring and artifacts in positron emission tomography (PET) imaging. Respiratory motion and cardiac motion during PET data acquisition can degrade quantitation performance by blurring images, leading to over-estimation of lesion volumes and under-estimation of lesion activity. Gating methods have been used to improve the quality of PET images. Typically, these methods need to use an external device to detect a biosignal, for example, a respiration waveform, electrocardiography (ECG), etc.

Recently, data-driven approaches have been developed for extracting the biosignal from raw PET data, or from reconstructed images. For example, a data-driven algorithm can first divide the PET acquisitions into small temporal frames, and then principal component analysis (PCA) or independent component analysis (ICA) can be applied on the frames. The biosignal can be extracted based on the data variation across all the frames.

For instance, where there is respiratory motion, normally the principal variation is caused by the respiratory motion. Thus, a respiratory signal can be modeled by the first component of the PCA. Once the respiratory motion is estimated, the PET data can be binned and reconstructed into multiple gates (for visualizing the motion) or a single gate (for generation of a single, motion-reduced image).

Though multiple gates can be generated by phase or amplitude gating, a single gate is still preferred for clinical image reviewing. Normally, the single gate is selected to align with the quiescent phase around end-expiration. That is, a certain phase of each respiratory cycle is selected to generate the gated image. However, due to the irregular respiratory motion, this conventional quiescent phase gating approach is not always optimal.

Therefore, it is desirable to address these and other deficiencies of current approaches.

SUMMARY

The present disclosure relates to a method for performing single gating in a positron emission tomography (PET) system. The method includes receiving list-mode data acquired by scanning an imaging object using the PET system, the list-mode data being affected by quasi-periodic motion of the imaging object. The method further includes producing a plurality of vectors based on the received list-mode data. The method also includes generating a reference vector based on the produced plurality of vectors. The method still further includes selecting, from the produced plurality of vectors, a set of vectors corresponding to a single gate, based on respective differences compared with the generated reference vector. Additionally, the method includes generating an image of the imaging object based on the selected set of vectors.

The disclosure additionally relates to an apparatus for performing single gating in a positron emission tomography (PET) system. The apparatus includes processing circuitry configured to: receive list-mode data acquired by scanning an imaging object using the PET system, the list-mode data being affected by quasi-periodic motion of the imaging object; produce a plurality of vectors based on the received list-mode data; generate a reference vector based on the produced plurality of vectors; select, from the produced plurality of vectors, a set of vectors corresponding to a single gate, based on respective differences compared with the generated reference vector; and generate an image of the imaging object based on the selected set of vectors.

Note that this summary section does not specify every embodiment and/or incrementally novel aspect of the present disclosure or claimed invention. Instead, the summary only provides a preliminary discussion of different embodiments and corresponding points of novelty. For additional details and/or possible perspectives of the disclosure and embodiments, the reader is directed to the Detailed Description section and corresponding figures of the present disclosure as further discussed below.

BRIEF DESCRIPTION OF THE DRAWINGS

Various embodiments of this disclosure that are proposed as examples will be described in detail with reference to the following figures, wherein like numerals reference like elements, and wherein:

FIG. 6 shows a flow chart of a single gate generating process according to one embodiment of the present disclosure;

FIG. 8 shows a flow chart of a single gate generating process according to one embodiment of the present disclosure;

FIG. 10 shows a flow chart of a single gate generating process according to one embodiment of the present disclosure;

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting.

For example, the order of discussion of the different steps as described herein has been presented for the sake of clarity. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present disclosure can be embodied and viewed in many different ways.

Furthermore, as used herein, the words "a," "an," and the like generally carry a meaning of "one or more," unless stated otherwise.

Numerous modifications and variations are possible in light of the above teachings. It is therefore to be understood that within the scope of the appended claims, the disclosure can be practiced otherwise than as specifically described herein.

Note that while the following embodiments are described in the context of respiratory gating, it is not meant to be restrictive. One skilled in the art will recognize that the concepts and principles discussed can be extended to other gating applications, such as cardiac gating, for example.

Figure 1:
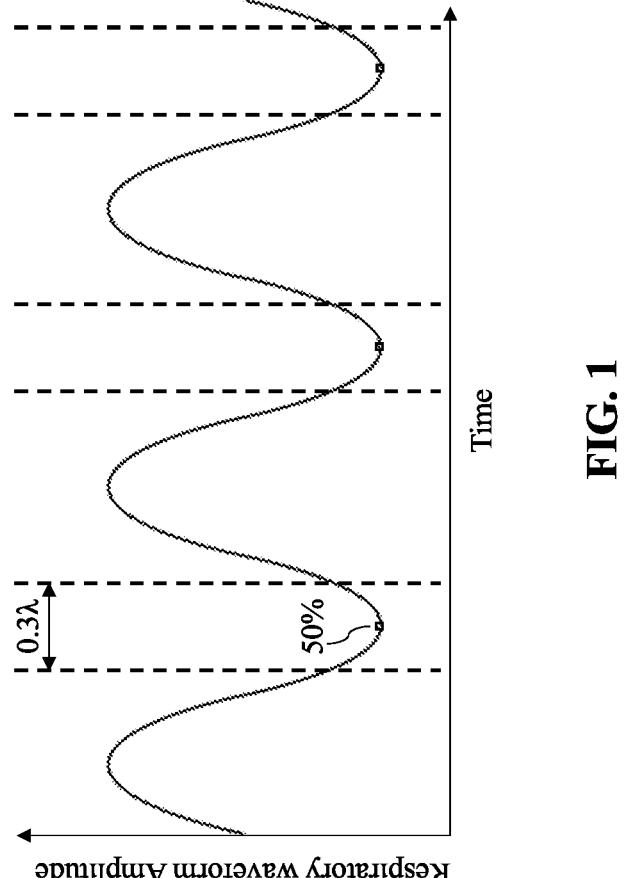
FIG. 1 shows a conventional phase-based gating approach that divides the PET data into a single quiescent phase for each respiratory cycle.

FIG. 1 shows a conventional fixed-phase data-driven gating approach for PET data, which divides the data into a single quiescent phase for each respiratory cycle. In this approach, a phase offset (e.g., a 50% offset from the end-inspiration phase) is selected to choose a frame that captures the quiescent breathing phase, which is roughly halfway through the breathing cycle. Then, a time span of data is extracted around that point. For example, the time span can be +/−15% of the breathing cycle, allowing a total of 30% of the original data to be used in reconstruction of the final image. However, since patients often exhibit irregular breathing patterns, it might not always be optimal to select the time span of data around the fixed phase offset from each breathing cycle.

Figure 4:
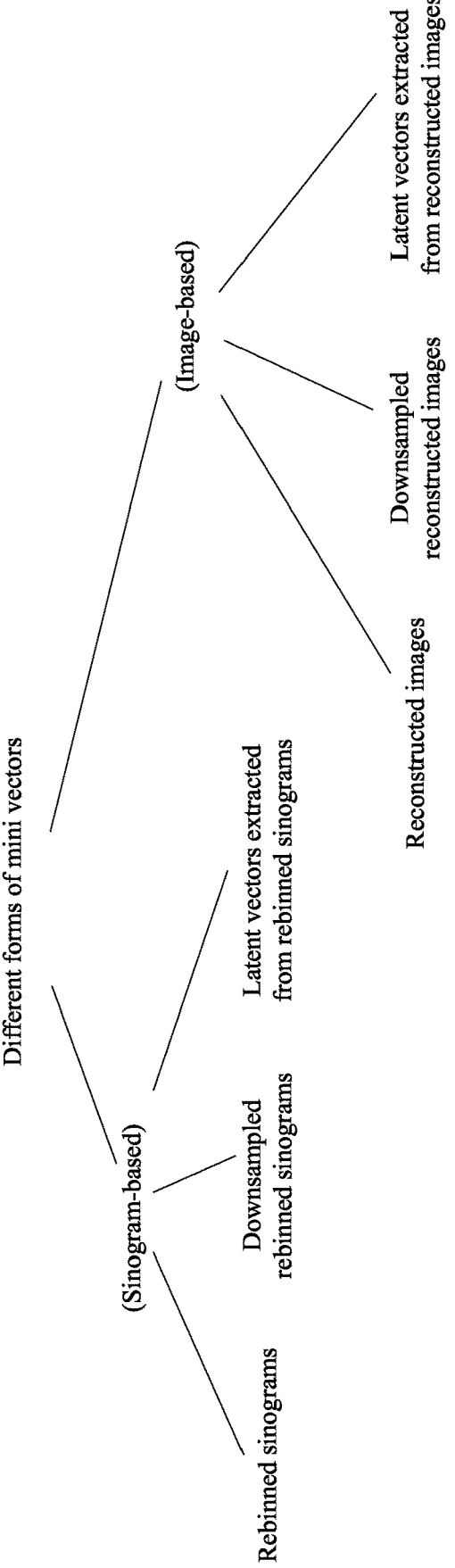
FIG. 4 shows different formats of mini vectors according to embodiments of the present disclosure.

The present disclosure provides embodiments of a data driven approach for generating single gating from PET list-mode data. The list-mode data can be divided into a sequence of frames with a short temporal length, referred to as "mini frames" below. The mini frames can be used to produce intermediate data, referred to as "mini vectors" below. These mini vectors can take various forms, as shown in FIG. 4.

A single frame with minimal motion blur can be obtained through processing of the mini vectors. The processing of the mini vectors can include, firstly, calculating a reference vector by averaging vectors corresponding to a specific target phase of the respiratory cycle, for example. Secondly, data that is most similar to the target vector can be identified by determining those time frames that have corresponding mini vectors closest to the reference vector.

By combining data with similar features, the accuracy of the single gating process can be enhanced, even if the respiratory motion is irregular. This is because selecting data with similar features increases the probability that motion is negligible or minimal, thereby improving the quality of the final image.

Figure 2:
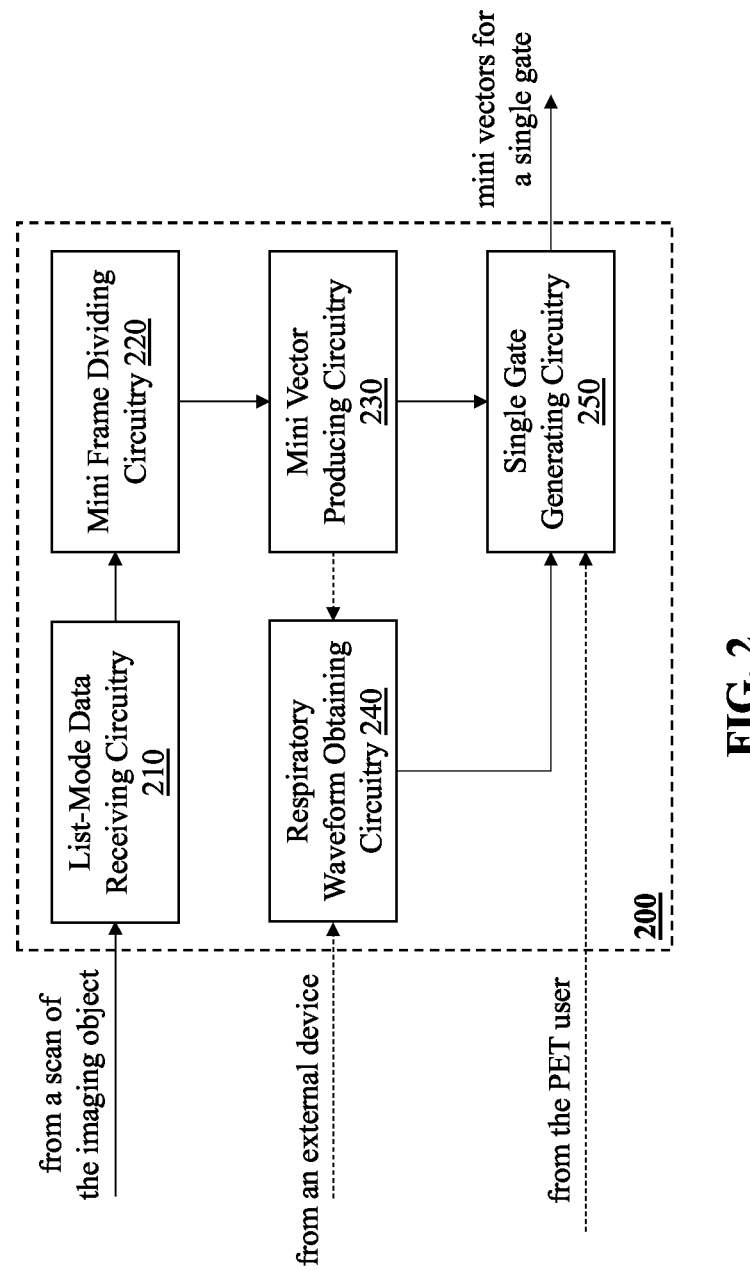
FIG. 2 shows a block diagram of a single gating apparatus according to embodiments of the present disclosure.

FIG. 2 shows a block diagram of a single gating apparatus 200 according to embodiments of the disclosure. The single gating apparatus 200 includes list-mode data receiving circuitry 210, mini frame dividing circuitry 220, mini vector producing circuitry 230, respiratory waveform obtaining circuitry 240, and single gate generating circuitry 250.

The list-mode data receiving circuitry 210 receives list-mode data acquired by scanning the imaging object using the PET system, and provides the received list-mode data to the mini frame dividing circuitry 220.

The mini frame dividing circuitry 220 divides the received list-mode data into short segments, i.e., the mini frames, which are then sent to the mini vector producing circuitry 230. The mini frames can have a short temporal length, for example, 0.1 second.

Based on the mini frames, the mini vector producing circuitry 230 produces mini vectors (the process will be described below with reference to FIG. 4) and sends them to the single gate generating circuitry 250. Optionally, the mini vector producing circuitry 230 can also send the produced mini vectors to the respiratory waveform obtaining circuitry 240.

The respiratory waveform obtaining circuitry 240 obtains the waveform of the respiratory motion of the imaging object during the scanning. In one embodiment, the respiratory waveform obtaining circuitry 240 can receive the respiratory waveform from an external device (not shown in FIG. 2). In another embodiment, the respiratory waveform obtaining circuitry 240 can derive the respiratory waveform based on the mini vectors received from the mini vector producing circuitry 230.

For example, the respiratory waveform obtaining circuitry 240 can use techniques such as PCA and ICA to extract the respiratory waveform from the mini vectors. This approach eliminates the need for the use of an external motion tracker, the need to synchronize the external motion tracker with the PET scanner, and the need for the stable use of such a motion tracker, even when the patient's breathing pattern or overall motion changes significantly.

Based on the respiratory waveform received from the respiratory waveform obtaining circuitry 240, the single gate generating circuitry 250 selects a subset of the mini vectors received from the mini vector producing circuitry 230 to generate a set of mini vectors for a single gate. This set of mini vectors can be used to perform image reconstruction that is less affected by motion artifacts.

Figure 3:
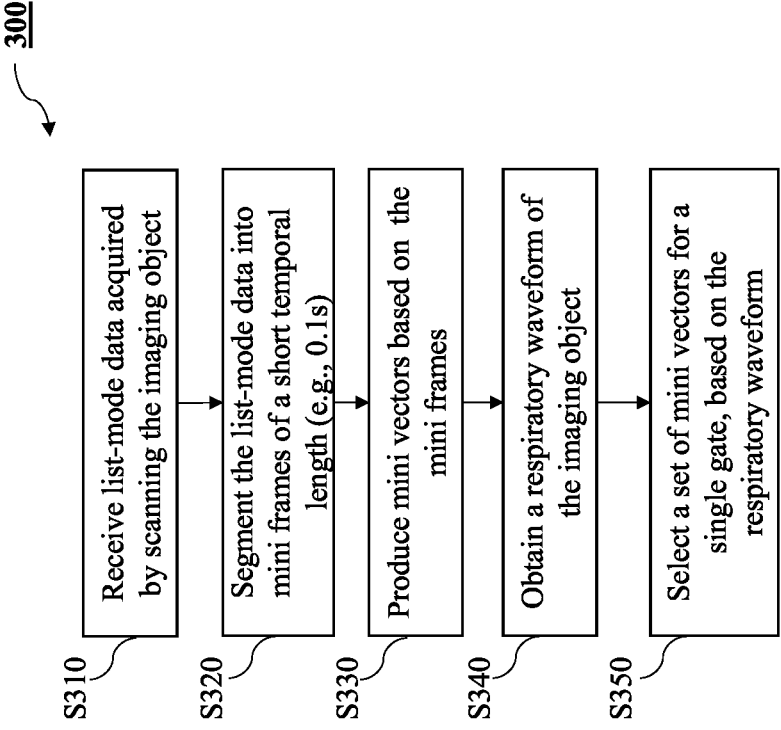
FIG. 3 shows a flow chart of a single gating process according to embodiments of the present disclosure.

FIG. 3 shows a flow chart of a single gating process 300 according to embodiments of the present disclosure. In step S310, list-mode data acquired by scanning the imaging object using the PET system is received. In step S320, the list-mode data can be segmented into the mini frames.

For instance, consider a scenario where a patient's regular breathing cycle lasts 3 seconds. A data acquisition session can capture approximately 30 breathing cycles. Consequently, the resulting list-mode data spanning a duration of 90 seconds can be divided into 900 mini frames, each with a duration of 0.1 second, for example. Alternatively, the mini frames can be designed to have longer durations with some degree of overlap. This approach can reduce the noise in each mini frame, so as to make the respiratory waveform obtained become more stable and accurate.

In step S330, mini vectors can be produced based on the mini frames. In this disclosure, the term "mini vectors" is used to refer to a collection of intermediate data obtained by processing the mini frames. As shown in FIG. 4 and described below, these mini vectors can take various forms, including sinograms, images, or latent vectors extracted from the sinograms or images, for example.

In step S340, a respiratory waveform of the imaging object during the scan is obtained. As described above, the respiratory waveform can be received from an external motion tracker, or can be estimated by analyzing the mini vectors.

In step S350, a set of mini vectors is selected for a single gate, among the mini vectors, based on the respiratory waveform obtained in step S340. The selected set of mini vectors can then be used to produce a motion-blur-free image of the imaging object.

FIG. 4 illustrates six possible forms of mini vectors according to embodiments of the present disclosure. There are multiple methods available for processing the mini frames to generate the mini vectors. As one approach, the mini frames can be rebinned into sinograms, which are used as the mini vectors. Alternatively, the mini frames can be rebinned into sinograms and subsequently downsampled to produce downsampled sinograms as the mini vectors. Another approach including applying an autoencoder to the sinograms to generate latent vectors as the mini vectors.

Image-based mini vectors can be used instead of the sinogram-based ones. In this case, the mini frames can be reconstructed into images, which serve as the mini vectors. Additionally, the mini frames can be reconstructed into images and then downsampled, resulting in downsampled images that are used as the mini vectors. Similarly, an autoencoder can be applied to the images reconstructed from the mini frames, so as to generate latent vectors as the mini vectors. It should be noted that the sinogram-based and image-based mini vectors illustrated in FIG. 4 are not exhaustive, and there are other possible forms of mini vectors that can be used to implement the concepts of this disclosure.

Figure 5:
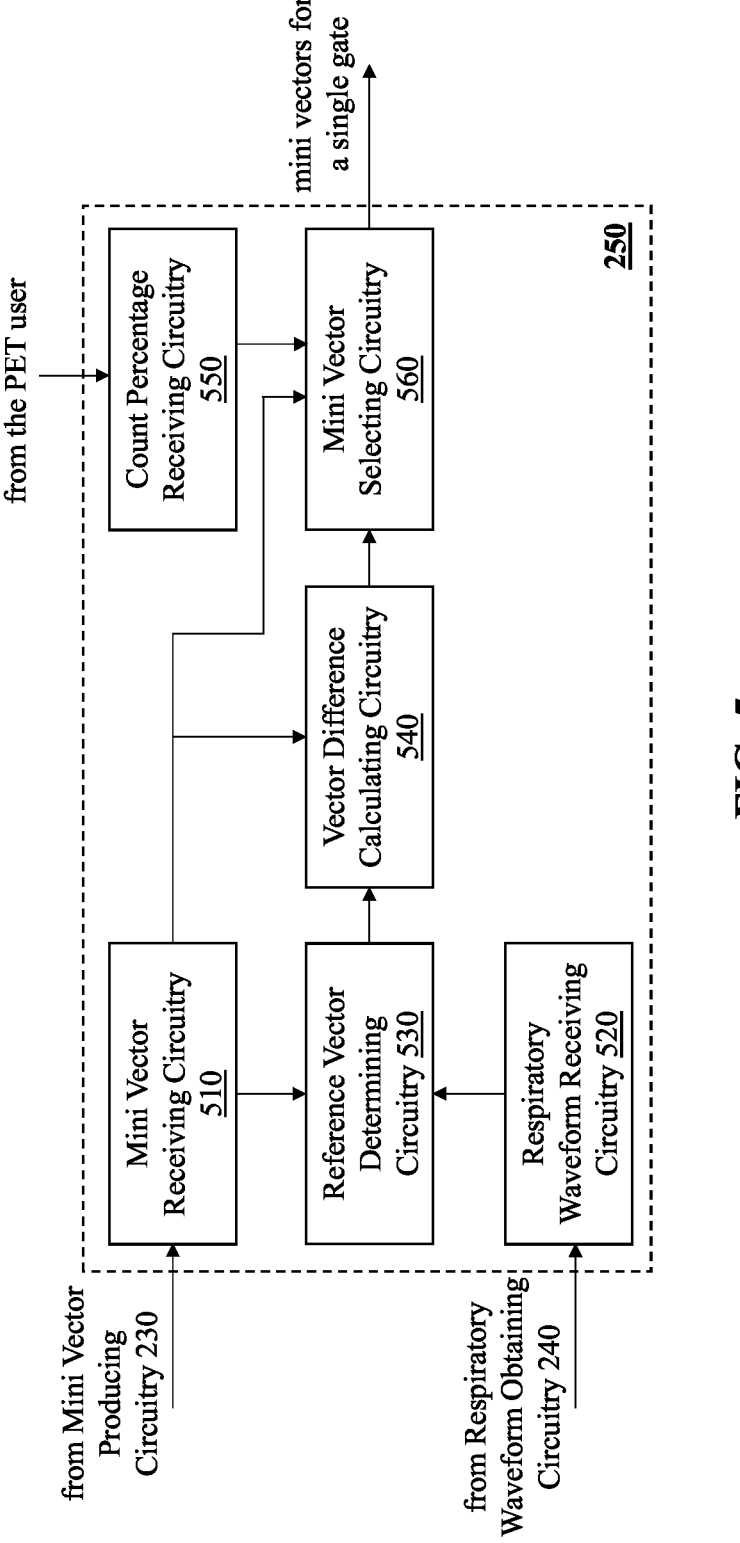
FIG. 5 shows a block diagram of single gate generating circuitry according to one embodiment of the present disclosure.

FIG. 5 shows a block diagram of single gate generating circuitry 250 according to one embodiment of the present disclosure. The single gate generating circuitry 250 includes mini vector receiving circuitry 510, respiratory waveform receiving circuitry 520, reference vector determining circuitry 530, vector difference calculating circuitry 540, count percentage receiving circuitry 550, and mini vector selecting circuitry 560.

The mini vector receiving circuitry 510 receives the mini vectors from the mini vector producing circuitry 230. As described before, the mini vectors can take various forms, including but not limited to sinogram-based and image-based ones.

The respiratory waveform receiving circuitry 520 received the respiratory waveform from the respiratory waveform obtaining circuitry 240.

The reference vector determining circuitry 530 receives the mini vectors from the mini vector receiving circuitry 510, and the respiratory waveform from the respiratory waveform receiving circuitry 520. Then, the reference vector determining circuitry 530 determines a reference vector, and sends it to the vector difference calculating circuitry 540.

The vector difference calculating circuitry 540 receives the mini vectors from the mini vector receiving circuitry 510, and the reference vector from the reference vector determining circuitry 530. The vector difference calculating circuitry 540 then calculates the difference between each of the mini vectors and the reference vector, and sends the calculated differences to the mini vector selecting circuitry 560.

The count percentage receiving circuitry 550 receives a count percentage (P %) from the user of the PET system, which specifies the proportion of the number of mini vectors to be selected for the single gate in relation to the total number of the mini vectors. The count percentage receiving circuitry 550 sends the received count percentage to the mini vector selecting circuitry 560.

Based on the respective differences compared with the reference vector, the mini vector selecting circuitry 560 identifies the first P % of the mini vectors that exhibit the smallest differences from the reference vector, so as to obtain a set of mini vectors for the single gate.

FIG. 6 shows a flow chart of a single gate generating process 600 according to one embodiment of the present disclosure. In step S610, the mini vectors produced based on the mini frames are received. In step S620, the respiratory waveform is received. As mentioned above, the respiratory waveform can be one generated through an analysis of the mini vectors, or it can be a respiratory waveform received directly from an external device.

In step S630, a reference vector is determined based on the mini vectors and the respiratory waveform. Various methods can be used to determine the reference vector.

For example, one approach can be to select the mini vectors from each respiratory cycle that correspond to a specific phase percentage of that cycle, such as 50%, as chosen by the user of the PET system. The selected mini vectors are then averaged to generate the reference vector.

Another option is to select the mini vectors from each respiratory cycle that align with the smallest amplitude point within that cycle. Then, the selected mini vectors can be averaged to generate the reference vector.

Additionally, the mini vectors from each respiratory cycle that correspond to a point having the smallest second-order amplitude derivative within that cycle can be selected. These selected mini vectors are then averaged to generate the reference vector. Note that the choice of derivative is not limited to the second-order amplitude derivative alone; the first-order amplitude derivative, or a combination of the first and second-order amplitude derivatives, can also be utilized.

In step S640, the difference between each mini vector and the reference vector is calculated. This difference can be calculated as a Euclidian distance, a covariance, a mean squared error (MSE), or a L1 norm between the two vectors.

In step S650, a count percentage (P %) is received from the user of the PET system. Then, in step S660, a set of mini vectors for a single gate is selected from the mini vectors, based on the differences and the count percentage. Specifically, the first P % of the mini vectors that have the smallest differences from the reference vector can be selected.

Figure 7:
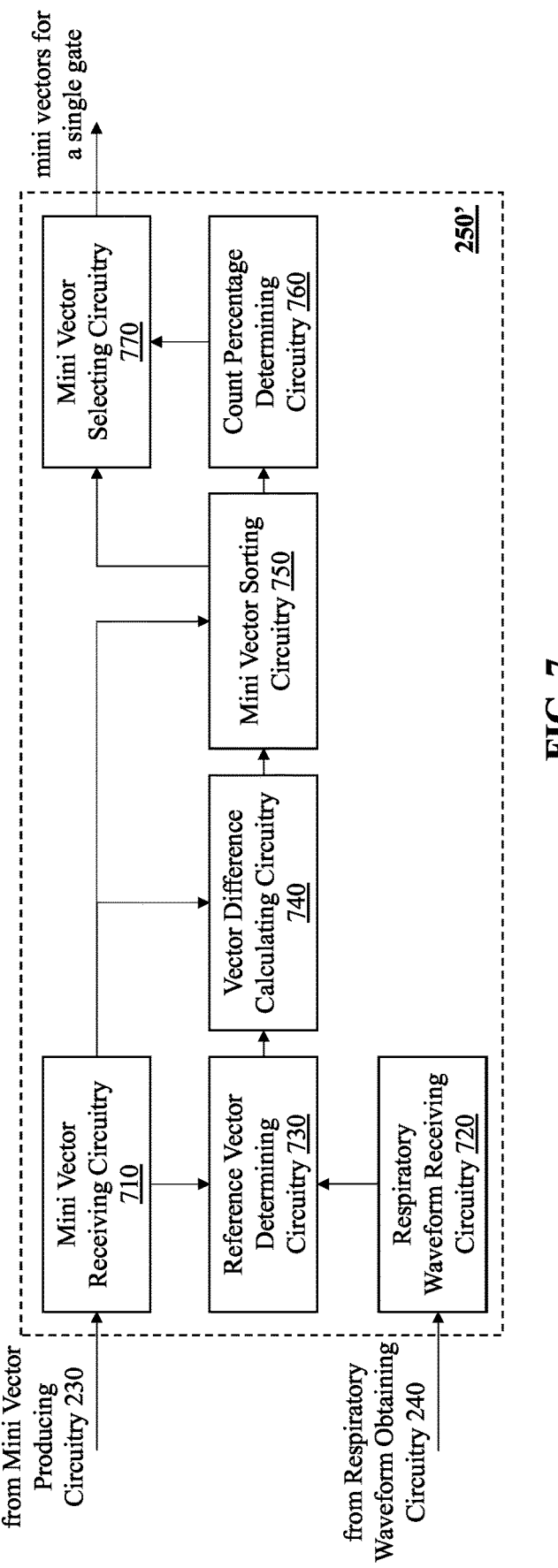
FIG. 7 shows a block diagram of single gate generating circuitry according to one embodiment of the present disclosure.

In the above embodiment, the count percentage is user-defined. However, in an alternative embodiment, the count percentage can be automatically determined. FIG. 7 shows a block diagram of single gate generating circuitry 250' according to one embodiment of the present disclosure. The structure of the single gate generating circuitry 250' in this embodiment is similar to that of the single gate generating circuitry 250 shown in FIG. 5, except for mini vector sorting circuitry 750, count percentage determining circuitry 760, and mini vector selecting circuitry 770.

The mini vector sorting circuitry 750 receives the mini vectors from the mini vector receiving circuitry 710, and the differences from the vector difference calculating circuitry 740. Based on the respective differences between the mini vectors and the reference vector, the mini vector sorting circuitry 750 can sort the mini vectors to create a curve to be sent to the count percentage determining circuitry 760. This curve represents the correlation between a count percentage (as the independent variable) of the mini vectors and the corresponding variation (as the dependent variable) in the vector differences associated with that count percentage.

The count percentage determining circuitry 760 identifies a turning point on the curve to determine the count percentage (P'%) corresponding to the turning point. For example, the turning point can be a point on the curve where the variation of the vector differences shifts from a relatively gradual increase to a sharp increase as the count percentage increases.

Using the determined count percentage (P'%), the mini vector selecting circuitry 770 selects the first P'% of the mini vectors that exhibit the smallest differences compared with the reference vector, obtaining a set of mini vectors for the single gate.

FIG. 8 shows a flow chart of a single gate generating process 800 according to one embodiment of the present disclosure. The processes of steps S810, S820, S830, and S840 are the same as those of steps S610, S620, S630, and S640 of FIG. 6, and thus, duplicate description will be omitted.

In step S850, the mini vectors are sorted based on their respective differences compared with the reference vector, so as to create a curve representing the correlation between a count percentage of the mini vectors and the corresponding variation in the vector differences associated with that count percentage.

In step 860, a specific count percentage (P'%) is determined based on the sorting of the mini vectors. This count percentage (P'%) can correspond to a turning point on the curve where the variation of the vector differences transitions from a slow increase to a rapid increase, for example.

In step S870, a set of mini vectors are selected for a single gate, based on the determined count percentage. The selected set of mini vectors can be the first P'% of all the mini vectors that exhibit the smallest differences compared with the reference vector.

In the embodiments shown in FIGS. 5-8, one reference vector is determined. Advantageously, an initial set of reference vector candidates can be derived, and subsequently, an optimal one can be chosen to be used as the final reference vector.

Figure 9:
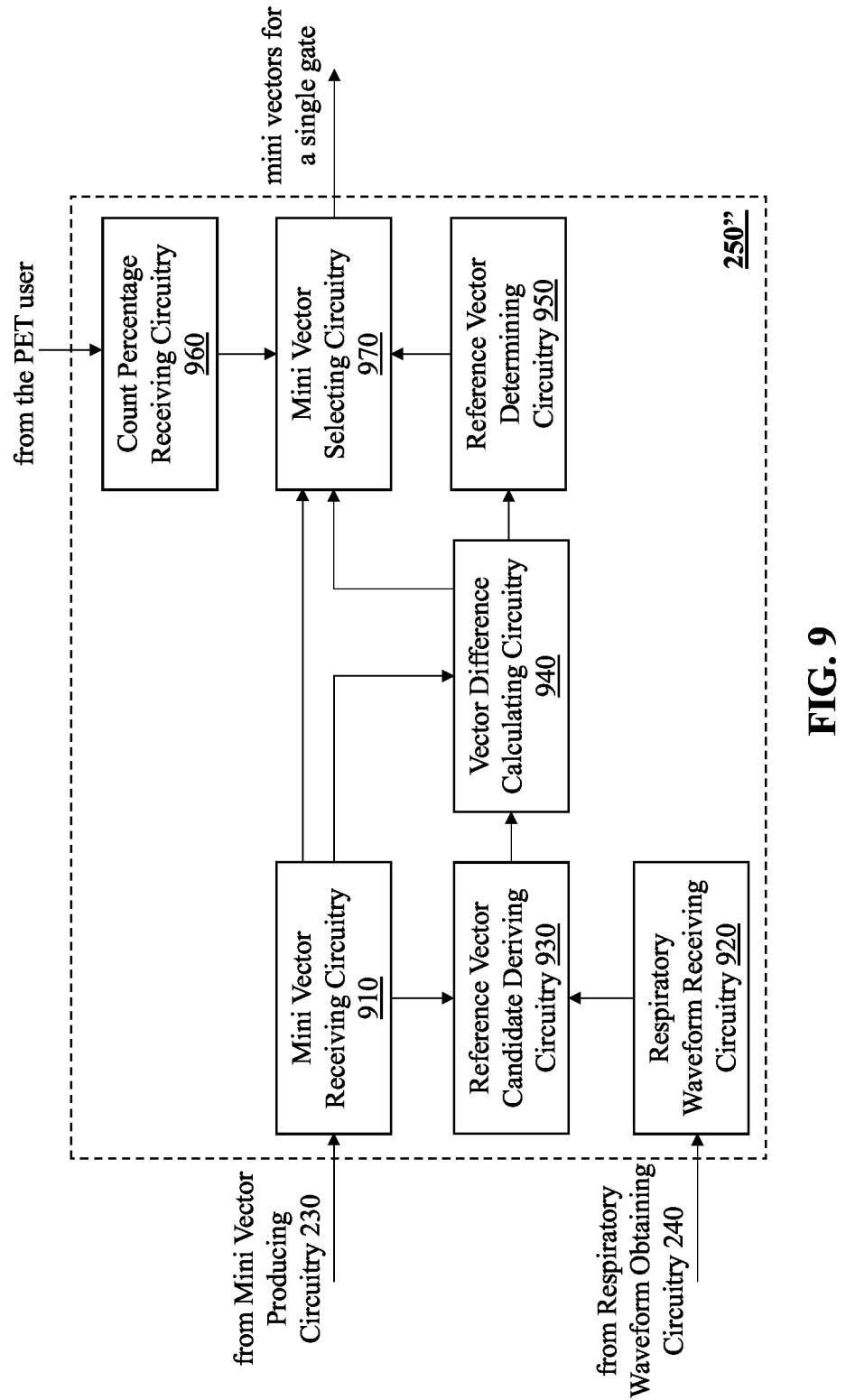
FIG. 9 shows a block diagram of single gate generating circuitry according to one embodiment of the present disclosure.

FIG. 9 shows a block diagram of single gate generating circuitry 250" according to one embodiment of the present disclosure. The single gate generating circuitry 250" includes mini vector receiving circuitry 910, respiratory waveform receiving circuitry 920, reference vector candidate deriving circuitry 930, vector difference calculating circuitry 940, reference vector determining circuitry 950, count percentage receiving circuitry 960, and mini vector selecting circuitry 970.

The functions of the mini vector receiving circuitry 910 and the respiratory waveform receiving circuitry 920 are the same as those of the mini vector receiving circuitry 510 and the respiratory waveform receiving circuitry 520 in FIG. 5.

The reference vector candidate deriving circuitry 930 derives multiple reference vector candidates based on multiple different criteria. For example, the mini vectors from each respiratory cycle that correspond to a specific phase percentage of that cycle, such as 30%, can be selected. The selected mini vectors are then averaged to generate a first reference vector candidate. Similarly, additional reference vector candidates corresponding to 40%, 50%, 60%, and 70% can be generated. Note that the phase percentages of 30%, 40%, 50%, 60%, and 70% are merely examples, and it is possible to generate more or fewer reference vector candidates based on other phase percentages, the smallest amplitude points within the respiratory cycles, and/or points having the smallest amplitude derivatives within the respiratory cycles, without departing from the spirit and scope of this disclosure.

The vector difference calculating circuitry 940 receives the reference vector candidates from the reference vector candidate deriving circuitry 930, and the mini vectors from the mini vector receiving circuitry 910. Then, the vector difference calculating circuitry 940 calculates respective vector differences of the mini vectors compared with each reference vector candidate, and sends them to the reference vector determining circuitry 950 and the mini vector selecting circuitry 970.

Based on the vector differences received from the vector difference calculating circuitry 940, the reference vector determining circuitry 950 chooses the final reference vector from the multiple reference vector candidates. For example, the reference vector determining circuitry 950 can calculate the mean of the vector differences related to each of the multiple reference vector candidates, and then select the candidate with the smallest mean.

The count percentage receiving circuitry 960 receives a count percentage (P %) from the user of the PET system, which specifies the proportion of the number of mini vectors to be selected for the single gate in relation to the total number of the mini vectors. The count percentage receiving circuitry 960 sends the received count percentage P % to the mini vector selecting circuitry 970.

Based on the respective differences compared with the final reference vector, the mini vector selecting circuitry 970 identifies the first P % of the mini vectors that exhibit the smallest differences from the final reference vector, so as to obtain a set of mini vectors for the single gate.

FIG. 10 shows a flow chart of a single gate generating process 1000 according to one embodiment of the present disclosure. Steps S1010, S1020, and S1060 correspond to steps S610, S620, and S650 of FIG. 6 and will not be redundantly described.

In step S1030, multiple reference vector candidates are derived based on the respiratory waveform. For example, each reference vector candidate can be generated based on a different phase percentage selected from a range of, e.g., 30%-70%, which may cover both the end-inspiration and end-expiration phases of the respiratory cycle. Note that this range is not restrictive, because other ranges covering only one of the end-inspiration and the end-expiration phases are also possible. Additionally, the desired range can be determined based on the concavity of the respiratory waveform. This approach allows coverage of various points or parts within the respiratory cycle, including but not limited to, the rising part of the waveform, the descending part of the waveform, the smallest amplitude point within the respiratory cycle, the largest amplitude point within the respiratory cycle, and the point having the smallest (or largest) first- or second-order amplitude derivative within the respiratory cycle, etc.

In step S1040, the vector differences of the mini vectors with respect to each of the reference vector candidates are calculated.

In step S1050, based on the vector differences calculated in step S1040, a reference vector candidate having the smallest averaged vector difference is identified as the final reference vector.

In step S1070, a set of mini vectors is selected for a single gate, based on the final reference vector determined in step S1050 and the count percentage P % received in step S1060. The selected set of mini vectors can be the first P % of the mini vectors that exhibit the smallest differences compared with the final reference vector.

Figures 11A, 11B, 11C:
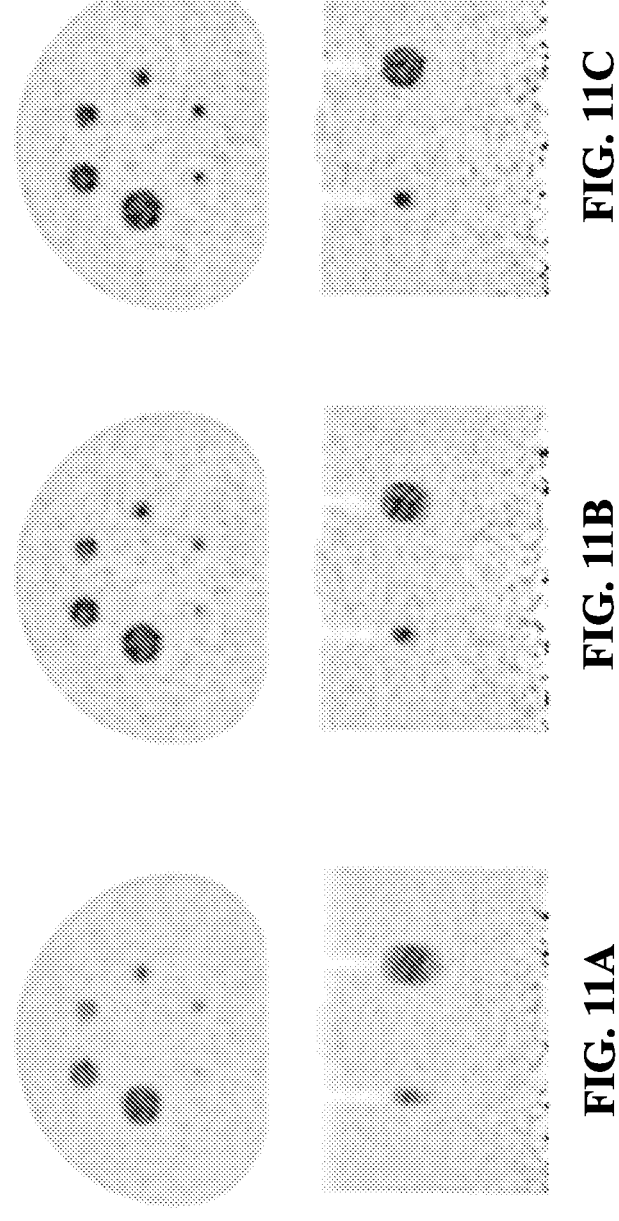
FIGS. 11A, 11B, and 11C show an ungated image, a quiescent phase gated image, and a single gated image according to one embodiment of the present disclosure of axial and coronal slices of a moving International Electrotechnical Commission (IEC) phantom.

FIGS. 11A, 11B, and 11C show an ungated image, a quiescent phase gated image, and a single gated image according to one embodiment of the present disclosure of axial and coronal slices of a moving IEC phantom. The IEC phantom has six spheres (d=10, 13, 17, 22, 28, 37 mm) with 4:1 contrast and moves axially based on programmed respiratory motion waveforms. As can be seen from FIGS. 11A-11C, the ungated and phase-gated images can lead to over-estimation of sphere volumes and under-estimation of sphere activities, while the single-gated approach in accordance with this disclosure generates an image closest to the ground truth.

The image quality of the non-gated image, the quiescent phase-gated image, and the single-gated image according to the embodiment of the present disclosure can be evaluated qualitatively. Table 1 below shows a comparison in terms of the contrast recovery coefficient (CRC) for the phantom data.

TABLE 1

| the CRC of all the six spheres for the ungated image, the quiescent phase-gated image, and the single-gated image of this disclosure | | | | | | |
|---|---|---|---|---|---|---|
| | 10 mm | 13 mm | 17 mm | 22 mm | 28 mm | 37 mm |
| Ungated | 25% | 39% | 56% | 67% | 78% | 83% |
| Quiescent Phase-gated | 36% | 53% | 76% | 83% | 91% | 93% |
| Single-Gated | 54% | 76% | 85% | 92% | 95% | 97% |

Figure 12:
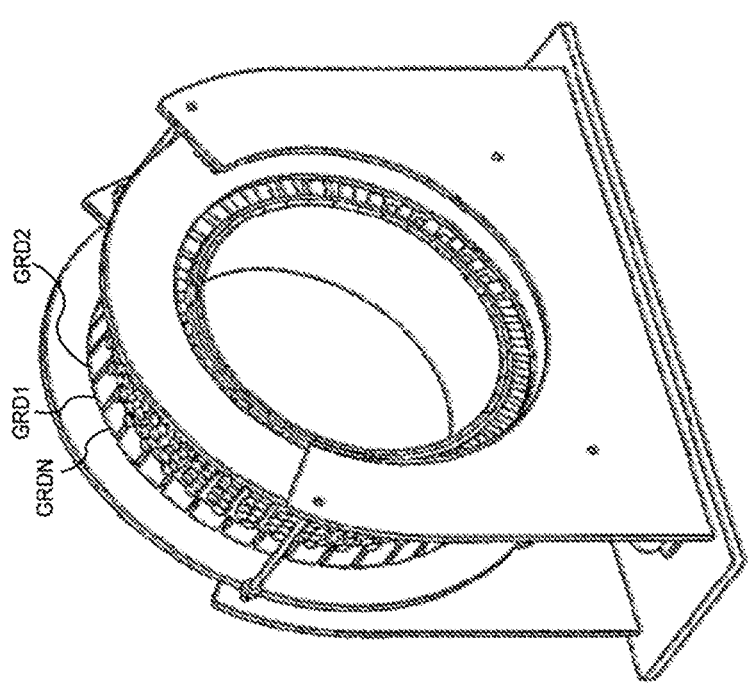
FIG. 12 is an illustration of a perspective view of a PET scanner apparatus according to embodiments of the present disclosure.
Figure 13:
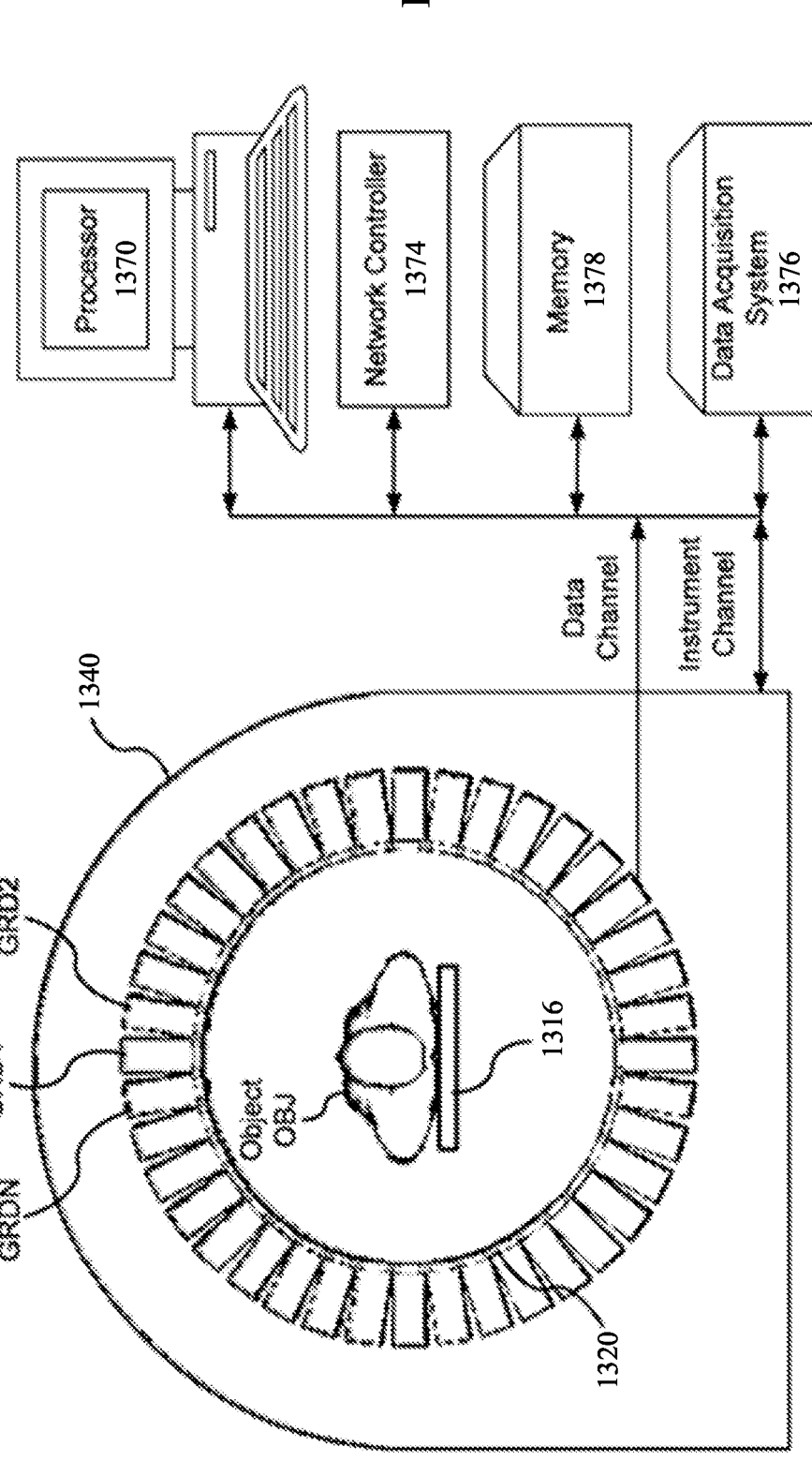
FIG. 13 is a schematic of a PET scanner apparatus and associated hardware, according to embodiments of the present disclosure.

FIGS. 12 and 13 illustrate an implementation in which a medical imaging system includes a PET scanner that can implement the methods described in this disclosure. The PET scanner includes a plurality of gamma-ray detectors (GRDs) (e.g., GRD1, GRD2, through GRDN) that are each configured as rectangular detector modules.

Each GRD can include a two-dimensional array of individual detector crystals, which absorb gamma radiation and emit scintillation photons. The scintillation photons can be detected by a two-dimensional array of photomultiplier tubes (PMTs) or silicon photomultipliers (SiPMs). A light guide can be disposed between the array of detector crystals and the photodetectors.

Each photodetector (e.g., PMT or SiPM) can produce an analog signal that indicates when scintillation events occur, and an energy of the gamma ray producing the detection event. Moreover, the photons emitted from one detector crystal can be detected by more than one photodetector, and, based on the analog signal produced at each photodetector, the detector crystal corresponding to the detection event can be determined using Anger logic and crystal decoding, for example.

FIG. 13 shows one example of the arrangement of the PET scanner, in which the object OBJ to be imaged rests on a table 1316 and the GRD modules GRD1 through GRDN are arranged circumferentially around the object OBJ and the table 1316. The GRDs can be fixedly connected to a circular component 1320 that is fixedly connected to a gantry 1340. The gantry 1340 houses many parts of the PET scanner. The gantry 1340 of the PET scanner also includes an open aperture through which the object OBJ and the table 1316 can pass, and gamma-rays emitted in opposite directions from the object OBJ due to an annihilation event can be detected by the GRDs and timing and energy information can be used to determine coincidences for gamma-ray pairs.

In FIG. 13, circuitry and hardware are also shown for acquiring, storing, processing, and distributing gamma-ray detection data. The circuitry and hardware include: a processor 1370, a network controller 1374, a memory 1378, and a data acquisition system (DAS) 1376. The PET scanner also includes a data channel that routes detection measurement results from the GRDs to the DAS 1376, the processor 1370, the memory 1378, and the network controller 1374. The data acquisition system 1376 can control the acquisition, digitization, and routing of the detection data from the detectors. In one implementation, the DAS 1376 controls the movement of the bed 1316. The processor 1370 performs functions including reconstructing images from the detection data, pre-reconstruction processing of the detection data, and post-reconstruction processing of the image data, as discussed herein.

The processor 1370 can be configured to perform various steps of the methods described herein and variations thereof. The processor 1370 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 1370 can execute a computer program including a set of computer-readable instructions that perform various steps of the described methods, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

The memory 1378 can be a hard disk drive, CD-ROM drive, DVD drive, FLASH drive, RAM, ROM or any other electronic storage known in the art.

The network controller 1374, such as an Intel Ethernet PRO network interface card from Intel Corporation of America, can interface between the various parts of the PET scanner. Additionally, the network controller 1374 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

In at least one of the above-exemplary embodiments, the reference vector is generated based on the plurality of latent vectors using the autoencoder. In one of the alternative embodiments, a reference vector can be generated directly from the signograms/PET images, instead of generating it from the plurality of latent vectors. In one embodiment, list-mode data set acquired in the +/−15% window of the breathing cycle, that is a larger data set than that for generating each of the plurality of latent vectors, can be input into an autoencoder to obtain the reference vector. You can train such an autoencoder as you train the autoencoder used in the above-exemplary embodiments. Please note that, the list-mode data set for the direct generation of reference vector, may cover entirety of the window. In other words, the list mode data set includes a piece of list-mode data acquired at a start time point of the window and includes a piece of list-mode data acquired at the end time point of the window. Alternatively, you can choose a window including a set of non-overlapping or overlapping sub-windows included in the +/−15% window of the breathing cycle. The specific target phase should also be in between the earliest time point of the set of sub-windows and the latest time point of the set of sub-windows.

The window in this embodiment is defined based on a phase, but you may also define the window based on a time from a specific point in a respiratory cycle or on an amplitude of the respiratory cycle. You may choose one of the phase-related, time-related or amplitude-related definition of the window for the reference vector generation. In this embodiment the window covers the same range in the respiratory cycle as the single gate, but you may choose broader or shorter range than the predetermined single gate.

In other embodiments, the above-described technology can also be adapted for other modalities, than positron emission tomography (PET) imaging system described above, including a single positron emission computed tomography (SPECT) imaging system, an X-ray computed tomography (CT) imaging system, a magnetic resonance (MR) imaging system, and an X-ray imaging system. In using other modalities, you can use scan data (for MR the scan data should be k-space data, and for X-ray imaging system the scan data should be X-ray image) for the latent vector generation and the reference vector generation. In yet another embodiments, you may also use camera receiving visible or infrared light to generate visible light images or infrared light images.

Also, in other embodiments, the above-described technology can also be applied to other types of quasi-periodic motions, than the respiratory (breathing) motion, including cardiac motion, with sufficiently long duration acquisition over several cardiac motion cycles.

In other embodiments, you may also use other types of feature vector, other than the latent vectors, including the motion characteristics. These types of feature vector can include compressed, segmented, or other alternate representations of images/sinogram/listmode data.

Embodiments of the present disclosure may also be as set forth in the following parentheticals.

(1) A method for performing single gating in a positron emission tomography (PET) system, the method comprising: receiving list-mode data acquired by scanning an imaging object using the PET system, the list-mode data being affected by quasi-periodic motion of the imaging object; producing a plurality of vectors based on the received list-mode data; generating a reference vector based on the produced plurality of vectors; selecting, from the produced plurality of vectors, a set of vectors corresponding to a single gate, based on respective differences compared with the generated reference vector; and generating an image of the imaging object based on the selected set of vectors.

(2) The method of (1), wherein the generating step further comprises: obtaining a motion waveform with respect to the quasi-periodic motion of the imaging object, the obtained motion waveform having a number of cycles, deriving, based on a predefined criterion, a first number of vectors from the produced plurality of vectors, each of the first number of vectors corresponding to one of the number of cycles of the obtained motion waveform, and calculating, as the generated reference vector, an average of the derived number of vectors.

(3) The method of (2), wherein the deriving step further comprises: identifying, as the derived first number of vectors, a second number of vectors from the produced plurality of vectors, each of the identified second number of vectors corresponding to a predetermined phase percentage within one of the number of cycles of the obtained motion waveform.

(4) The method of (2), wherein the deriving step further comprises: identifying, as the derived first number of vectors, a second number of vectors from the produced plurality of vectors, each of the second identified number of vectors corresponding to a smallest amplitude point within one of the number of cycles of the obtained motion waveform.

(5) The method of (2), wherein the deriving step further comprises: identifying, as the derived first number of vectors, a second number of vectors from the produced plurality of vectors, each of the second identified number of vectors corresponding to a point having a smallest derivative term within one of the number of cycles of the obtained motion waveform, the derivative term being a first-order derivative of the obtained motion waveform, a second-order derivative of the obtained motion waveform, or a combination thereof.

(6) The method of (1), wherein the selecting step further comprises: obtaining a count percentage (P %) indicating a ratio of a number of the selected set of vectors to a number of the produced plurality of vectors, and determining, as the selected set of vectors, a first P % of the produced plurality of vectors when ranked from smallest difference to largest difference, compared with the generated reference vector.

(7) The method of (6), wherein the obtaining step further comprises: receiving, as the obtained count percentage, a count percentage from a user of the PET system.

(8) The method of (6), wherein the obtaining step further comprises: sorting, based on the respective differences compared with the generated reference vector, the produced plurality of vectors to create a curve, the created curve representing a relationship between a count percentage of the produced plurality of vectors and a corresponding variation of the respective differences compared with the generated reference vector, identifying a turning point on the created curve, and deriving, as the obtained count percentage, a count percentage corresponding to the identified turning point on the created curve.

(9) The method of (2), wherein the generating step further comprises: generating multiple reference vector candidates based on multiple predefined criteria, obtaining a count percentage (P %) indicating a ratio of a number of the selected set of vectors to a number of the produced plurality of vectors, calculating, with respect to each of the multiple reference vector candidates, an averaged difference of a first P % of the produced plurality of vectors when ranked from smallest difference to largest difference, compared with the reference vector candidate, and determining, as the generated reference vector, one of the multiple reference vector candidates that has a smallest calculated averaged difference.

(10) The method of (1), wherein the respective differences compared with the generated reference vector are calculated as one of: a Euclidian distance compared with the generated reference vector, a covariance compared with the generated reference vector, a mean squared error (MSE) compared with the generated reference vector, and an L1 norm distance compared with the generated reference vector.

(11) The method of (2), wherein the producing step further comprises: dividing the received list-mode data into a plurality of segments; and creating, as the produced plurality of vectors, a plurality vectors based on the divided plurality of segments.

(12) The method of (11), wherein the creating step further comprises: creating, as the produced plurality of vectors, a plurality of sinograms based on the divided plurality of segments.

(13) The method of (11), wherein the creating step further comprises: creating a plurality of sinograms based on the divided plurality of segments, and performing downsampling on the created plurality of sinograms to obtain downsampled plurality of sinograms, as the produced plurality of vectors.

(14) The method of (11), wherein the creating step further comprises: creating a plurality of sinograms based on the divided plurality of segments, and extracting, as the produced plurality of vectors, a plurality of latent vectors from the created plurality of sinograms.

(15) The method of (11), wherein the creating step further comprises: reconstructing, as the produced plurality of vectors, a plurality of images based on the divided plurality of segments.

(16) The method of (11), wherein the creating step further comprises: reconstructing a plurality of images based on the divided plurality of segments, and performing downsampling on the reconstructed plurality of images to obtain downsampled plurality of vectors, as the produced plurality of vectors.

(17) The method of (11), wherein the creating step further comprises: reconstructing a plurality of images based on the divided plurality of segments, and extracting, as the produced plurality of vectors, a plurality of latent vectors from the reconstructed plurality of images.

(18) The method of (2), wherein the obtaining step further comprises: estimating, as the obtained motion waveform, a motion waveform by analyzing the produced plurality of vectors, or receiving, as the obtained motion waveform, a waveform from a device measuring the quasi-periodic motion of the imaging object.

(19) The method of (19), wherein the quasi-periodic motion of the imaging object is respiratory motion of the imaging object, or cardiac motion of the imaging object.

(20) An apparatus for performing single gating in a positron emission tomography (PET) system, the apparatus comprising processing circuitry configured to: receive list-mode data acquired by scanning an imaging object using the PET system, the list-mode data being affected by quasi-periodic motion of the imaging object; produce a plurality of vectors based on the received list-mode data; generate a reference vector based on the produced plurality of vectors; select, from the produced plurality of vectors, a set of vectors corresponding to a single gate, based on respective differences compared with the generated reference vector; and generate an image of the imaging object based on the selected set of vectors.

(21). A method for performing single gating in medical imaging system, the method comprising: receiving scan data acquired by scanning an imaging object using the medical imaging system, the scan data being affected by quasi-periodic motion of the imaging object; producing a plurality of vectors based on the received scan data; setting a time-related, phase-related or amplitude-related window, on quasi-periodic motion cycle of the imaging object during acquisition of the scan data, including a specific target phase; generating a reference vector based on a subset of the scan data, wherein the subset is acquired during the window; producing a plurality of vectors based on the received scan data; selecting a set of vectors corresponding to a single gate corresponding to the window and including the specific target phase, based on the generated reference vector; and generating an image of the imaging object based on the selected set of vectors.

(22) The method of (21), wherein the subset of scan data includes a piece of scan data acquired at a start time point of the window, and includes a piece of scan data acquired at the end time point of the window.

(23) The method of (21), wherein the window includes a set of sub-windows, wherein the specific target phase is in between the earliest time point of the set of sub-windows and the latest time point of the set of sub-windows.

(24) The method of (21), wherein the window covers the same range in the quasi-periodic motion cycle as the single gate.

(25) The method of (21), wherein the medical imaging system is at least one of a positron emission tomography (PET) imaging system, a single positron emission computed tomography (SPECT) imaging system, an X-ray computed tomography (CT) imaging system, a magnetic resonance (MR) imaging system, and an X-ray imaging system.

(26) The method of (21), wherein the quasi-periodic motion is at least one of a respiratory motion and a cardiac motion cycle.

Those skilled in the art will also understand that there can be many variations made to the operations of the techniques explained above while still achieving the same objectives of the disclosure. Such variations are intended to be covered by the scope of this disclosure. As such, the foregoing descriptions of embodiments of the disclosure are not intended to be limiting. Rather, any limitations to embodiments of the disclosure are presented in the following claims.

What is claimed is:

1. A method for processing list-mode data obtained by a positron emission tomography (PET) system scanning an imaging object, the method comprising:

dividing the list-mode data into a plurality of sets of data;

generating a first plurality of vectors corresponding to a different one of the plurality of sets of data;

generating a reference vector corresponding to a target respiration phase included in a cycle of a respiration of the imaging object based on a second plurality of vectors included in the first plurality of vectors, each of the second plurality of vectors corresponding to the target respiration phase;

selecting, from the plurality of sets of data, a set of data to be used to reconstruct an image, based on respective differences between the generated reference vector and the first plurality of vectors; and generating the image based on the selected set of data.

2. The method of claim 1, further comprising:

obtaining information indicating a waveform of respiration of the imaging object, the waveform having a plurality of cycles, wherein each of the second plurality of vectors corresponding to a different one of the target respiration phase in the plurality of cycles of the waveform, and wherein the reference vector is generated by calculating an average of the second plurality of vectors.

3. The method of claim 2, wherein the target respiration phase includes:

a smallest amplitude point in a cycle of the waveform.

4. The method of claim 2, wherein the target respiration phase includes:

a point having a smallest derivative term in a cycle of the waveform, the derivative term being a first-order derivative of the waveform, a second-order derivative of the waveform, or a combination thereof.

5. The method of claim 2, wherein the information is acquired by a sensor detecting the respiration.

6. The method of claim 1, further comprising:

obtaining a count percentage (P %) indicating a ratio of a number of the selected set of data to a number of the plurality of sets of data each corresponding to a different one of the first plurality of vectors, and determining, as the selected set of data, a first P % of the plurality of sets of data when ranked from smallest difference to largest difference, compared with the reference vector.

7. The method of claim 6, further comprising:

sorting, based on the respective differences, the first plurality of vectors to create a curve, the created curve representing a relationship between a count percentage of the first plurality of vectors and a corresponding variation of the respective differences, identifying a turning point on the created curve, and deriving, as the obtained count percentage, a count percentage corresponding to the identified turning point on the created curve.

8. The method of claim 1, wherein the target respiration phase is designated by a user of the PET system.

9. The method of claim 1, wherein the respective differences are calculated as one of:

a Euclidian distance between the generated reference vector and the first plurality of vector, a covariance between the generated reference vector and the first plurality of vector, a mean squared error (MSE) between the generated reference vector and the first plurality of vector, and an L1 norm distance between the generated reference vector and the first plurality of vector.

10. The method of claim 1, further comprising generating a plurality of sinograms, each corresponding to a different one of the plurality of sets of data, wherein each of the first plurality of vectors indicates a different one of the plurality of sinograms.

11. The method of claim 1, wherein each of the plurality of vectors is a different one of a plurality of images reconstructed on the plurality of sets of data.

12. The method of claim 1, wherein the information is acquired by analyzing the first plurality of vectors.

13. The method of claim 1, further comprising generating a plurality of sinograms, each corresponding to a different one of the plurality of sets of data, wherein each of the first plurality of vectors indicates a different one of downsampled plurality of sinograms obtained by performing downsampling on the generated plurality of sinograms.

14. The method of claim 1, further comprising generating a plurality of sinograms, each corresponding to a different one of the plurality of sets of data, wherein each of the first plurality of vectors indicates a different one of a plurality of latent vectors extracted from the generated plurality of sinograms.

15. The method of claim 1, further comprising generating a plurality of images, each corresponding to a different one of the plurality of sets of data, wherein each of the plurality of vectors indicates a different one of downsampled plurality of images obtained by performing downsampling on the generated plurality of images.

16. The method of claim 1, further comprising generating a plurality of images, each corresponding to a different one of the plurality of sets of data, wherein each of the plurality of vectors indicates a different one of a plurality of latent vectors extracted from the generated plurality of images.

17. The method of claim 1, wherein the target respiration phase is a period included in the cycle of the respiration and a length of the period is shorter than a length of the cycle of the respiration.

18. An apparatus for processing list-mode data obtained by a positron emission tomography (PET) system scanning an imaging object, the apparatus comprising:

processing circuitry configured to divide the list-mode data into a plurality of sets of data;

generate a first plurality of vectors corresponding to a different one of the plurality of sets of data;

generate a reference vector corresponding to a target respiration phase included in a cycle of a respiration of the imaging object based on a second plurality of vectors included in the first plurality of vectors, each of the second plurality of vectors corresponding to the target respiration phase;

select, from the plurality of sets of data, a set of data to be used to reconstruct an image, based on respective differences between the generated reference vector and the first plurality of vectors; and generate the image based on the selected set of data.

* * * * *